United States Patent [19]

Randklev

[11] Patent Number: 4,906,185

[45] Date of Patent: Mar. 6, 1990

[54] ORTHODONTIC BRACKET ADHESIVE AND ABRASIVE FOR REMOVAL THEREOF

[75] Inventor: Ronald M. Randklev, St. Paul, Minn.

[73] Assignee: Minnesota Mining and Manufacturing Company, St. Paul, Minn.

[21] Appl. No.: 15,662

[22] Filed: Feb. 17, 1987

Related U.S. Application Data

[60] Continuation of Ser. No. 694,477, Jan. 23, 1985, Pat. No. 4,695,251, which is a continuation of Ser. No. 559,401, Dec. 8, 1983, abandoned, which is a division of Ser. No. 406,500, Aug. 9, 1982, Pat. No. 4,435,160, which is a continuation of Ser. No. 172,218, Jul. 25, 1980, abandoned, which is a continuation-in-part of Ser. No. 137,631, Apr. 7, 1980, abandoned.

[51] Int. Cl.$^4$ ............................ A61D 5/00; B24B 1/00
[52] U.S. Cl. ............................................. 433/8; 51/295
[58] Field of Search ............................... 51/295; 433/8

[56] References Cited

U.S. PATENT DOCUMENTS

| 4,138,229 | 2/1979 | Tadokoro | 51/295 |
| 4,435,160 | 3/1984 | Randklev | 106/35 |
| 4,695,251 | 9/1987 | Randklev | 433/8 |

Primary Examiner—Theodore Morris
Attorney, Agent, or Firm—Donald M. Sell; Walter N. Kirn; David R. Cleveland

[57] ABSTRACT

A manufacture for orthodontic bracket application and removal, employing an orthodontic bracket adhesive containing a non-toxic, inorganic filler which is insoluble in mouth fluids and has a Mohs hardness less than about 4.5, together with an abrasive for removal of the adhesive. The abrasive is a non-toxic, inorganic material having a Mohs hardness greater than that of the adhesive filler but less than about 5.

9 Claims, No Drawings

ORTHODONTIC BRACKET ADHESIVE AND ABRASIVE FOR REMOVAL THEREOF

This application is a continuation of U.S. patent application Ser. No. 694,477, filed Jan. 23, 1985, which is in turn a continuation of U.S. patent application Ser. No. 559,401, filed Dec. 8, 1983, now abandoned, which is in turn a division of U.S. patent application Ser. No. 406,500, filed Aug. 9, 1982, now U.S. Pat. No. 4,435,160, which in turn is a continuation of U.S. patent application Ser. No. 172,218, filed July 25, 1980, now abandoned which is in turn a continuation-in-part of U.S. patent application Ser. No. 137,631, filed Apr. 7, 1980 now abandoned.

TECHNICAL FIELD

This invention relates to a packaged system for applying and removing orthodontic brackets. The invention also relates to orthodontic bracket adhesives, and to abrasives for removal of those adhesives. In addition, this invention relates to shaped abrasive forms useful in general dental work. This invention also relates to a method for applying and removing orthodontic brackets.

BACKGROUND ART

In the practice of orthodontic medicine, the position of teeth within the mouth is altered by anchoring tension wires to two or more teeth and applying sustained, steady pressure to the teeth to be moved. Tension wires are attached to individual teeth by surrounding the tooth with a band or by cementing a bracket to the tooth using an adhesive. If bands are used, they must be stocked by the orthodontist in many sizes. Also, bands tend to promote dental caries adjacent to the band.

Orthodontic brackets have become popular because they are simpler to apply to teeth than bands, see Retief and Denys, "Finishing of Enamel Surfaces After Debonding of Orthodontic Attachments", The Angle Orthodontist, Vol. 49, No. 1, pp. 1-10 (January 1979). After treatment, the bracket is removed from the tooth using orthodontic pliers or ligature cutters, and any residual adhesive is removed by grinding or scraping.

Early work with bracket adhesives dealt with means for improving the bond between the tooth and bracket in order to prevent inadvertent early failure of the adhesive bond. However, with improvements in tooth preparation, formulation of the adhesive, and construction of brackets, early bond failure is no longer a major problem. Instead, attention has now focused on techniques for minimizing tooth enamel damage when the bracket and any residual adhesive is removed. Modifications in dental technique designed to reduce such damage are described in Retief and Denys, id; Burapavong and Apfel, "Enamel Surface Characteristics on Removal of Bonded Orthodontic Brackets", Am. J. Orthod., Vol. 74, No. 2, pp. 176-187 (August 1978); Bennett, Schoen and Going, "Alterations of the Enamel Surface Following Direct-Bonded Bracket Therapy", Journal of Pedodontics, Vol. 4, No. 2, pp. 99-113 (Winter 1979); and Zachrisson and Arthun, "Enamel Surface Appearance After Various Debonding Techniques", Am. J. Orthod., Vol. 75, No. 2, pp. 121-137 (February 1979).

Studies have indicated that tooth preparation (by acid etching), removal of the bracket and adhesive, and polishing the tooth surface typically removes from about 43 to 56 microns of tooth enamel, see Fitzpatrick and Way, American Journal of Orthodontics, Vol. 72, No. 6, pp. 671-680 (December 1977) and Brown and Way, American Journal of Orthodontics, Vol. 74, No. 6, pp. 663-671 (December 1978). Although a loss of 55 microns of enamel represents only about 3 percent of the total enamel thickness of 1500 to 2000 microns, the highest concentration of fluoride is contained in the outer 20 microns of enamel. Also, any gouges or scratches which occur during removal may lead to later plaque and caries formation at the site of the scratch. Current recommendations for minimization of enamel damage are to use a tungsten carbide burr at low speed in Zachrisson and Arthun, id, a green rubber wheel (contraindicated somewhat due to generation of heat) in Gwinnett and Gorelick, Am. J. Orthod., Vol. 71, No. 6, pp. 651-665 (June 1977), or a low viscosity unfilled resin with a wire mesh base bracket (contraindicated somewhat due to undesirable slippage and shifting or the bracket on the tooth during curing) in Dogon and Moin, "An Evaluation of Shear Strength Measurements of Unfilled and Filled Resin Combinations", Am. J. Orthod., Vol. 74, No. 5, pp. 531-536 (November 1978). These references indicate that a need exists for an orthodontic bracket adhesive system which can be removed without excessive damage to tooth enamel.

Existing orthodontic bracket adhesives are generally made from binder, filler, and compounding and coloring adjuvants. Typically, the binders are the same as the binders used in tooth filling materials (i.e., dental restorative resins), such as the diglycidyl methacrylate adduct of epoxy resin (BIS-GMA) described in U.S. Pat. No. 3,066,112.

The fillers used in orthodontic bracket adhesive impart a sufficient viscosity to the adhesive to make it readily workable in the mouth. Without such a filler, the adhesive or the bracket is prone to slippage prior to cure. The fillers used in orthodontic bracket adhesives are generally also used in some dental restorative resins and include quartz, silica gel, aluminum silicate, silica, glass beads, aluminum oxide, titanium dioxide, zirconia, spodumene, lithium aluminum silicate, barium aluminum silicate, and silicate or phosphate glasses, see U.S. Pat. Nos. 3,625,916, 3,629,187, 3,709,866, 3,895,445, 4,010,545, and 4,063,360, and U.K. Published Patent Application No. 2,006,792 A. Some references have suggested using lower amounts of filler in an orthodontic bracket adhesive than the amounts typically used in those resotrative resins containing such fillers in order to ease removal of excess adhesive, see Gwinnett and Gorelick, id, Retief and Denys, id, and U.S. Pat. No. 3,629,187. However, removal of residual adhesive containing these fillers still can lead to damage to tooth enamel, because hardened tools must be used to grind away the excess adhesive.

The hardness of tooth enamel, measured upon the Mohs scale of hardness, is approximately 4.5 to 5, depending upon the age and location of the tooth. The fillers used in currently marketed orthodontic bracket adhesives have a Mohs hardness well in excess of this value. Consequently, yet harder abrasives must be used to remove such adhesives. Currently used abrasives include silicon carbide, diamond, stainless steel, aluminum oxide, and pumice. Such abrasives are described, for example, in Greener, Harcourt and Lautenschlager, "Materials Science in Dentistry", Williams & Wilkins, Baltimore (1972) at, e.g. pp. 379-383, Craig, O'Brien and Powers, "Dental Materials, Properties and Manipulation" Mosby, St. Louis (1979) at e.g. Chapter 6, and Anderson, "Applied Dental Materials", Blackwell, Oxford (1972) at, e.g. Chapter 29. All of these abrasives readily abrade tooth enamel.

In U.S. Pat. No. 4,141,144 (Lustgarten) there are described compositions for use as "paint-on" tooth veneers and direct filling materials, said to be useful for matching the hue and lustre of treated teeth with the hue and lustre of untreated teeth. Such compositions contain about 1 to 85 percent by weight muscovite mica flakes having an average size of less than about 50 microns. In such compositions some or all of the muscovite mica flakes are preferably coated with a continuous layer of $TiO_2$ or $ZrO_2$ (which coating materials have Mohs hardnesses of 5½ to 6½ and 7 to 7½ respectively), or BiOCl (which coating material has an unreported Mohs hardness, due perhaps to the commercial unavailability of crystalline BiOCl in a crystal size sufficient to allow Mohs hardness testing to be carried out). Also, such compositions preferably contain inorganic filler such as silica, glass beads, aluminum oxide, fused silica, fused or crystalline quartz, or the like (which inorganic fillers have generally high Mohs hardnesses, e.g., 7 or more). Such compositions therefore preferably contain inorganic materials whose surfaces are harder than tooth enamel. In the only example in Lustgarten in which uncoated mica is used and coated mica and inorganic filler are excluded (Viz., Example 14) about 22 percent by volume (about 39 to 41 percent by weight) uncoated muscovite mica was combined with methyl methacrylate to form a thin, yellowish 1.5 mm thick cured slab which was used in various optical comparison tests.

Dental restorative resins containing a filler having a Mohs hardness of 3 to 5 have been described as offering good wear resistance and polishability in U.S. Pat. No. 4,020,557, and dental restorative resins containing a rod-like filler having a Mohs hardness of 3.5 to 6 (such as calcium silicate) have been described as offering a resin with good strength and workability in Australian Patent Specification No. 50674/73. These references do not suggest the use of such fillers in an orthodontic bracket adhesive and abrasive system.

The above cited U.K. Published Patent Application No. 2,006,792 A states that an organic filler such as polymethyl methacrylate can be used in an orthodontic bracket adhesive. Such an organically filled adhesive has low hardness but insufficient tensile strength.

DISCLOSURE OF INVENTION

The present invention provides, in one aspect, a manufacture for orthodontic bracket application and removal, comprising:

(1) an orthodontic bracket adhesive composition, comprising a finely divided first inorganic material admixed with a polymerizable resin, said first inorganic material being non-toxic, essentially insoluble in mouth fluids, and having a Mohs hardness less than about 4.5;

(2) a solid abrasive tool, comprising a second inorganic material, said second inorganic material being non-toxic and having a Mohs hardness which is greater than the Mohs hardness of said first inorganic material and less than about 5.

The present invention also provides orthodontic bracket, adhesives, abrasives for the removal thereof, and a process for applying and removing orthodontic brackets.

DETAILED DESCRIPTION

A. Adhesive

In the practice of the present invention, the first inorganic material (i.e. the filler used in the adhesive) has a Mohs hardness less than about 4.5, preferably less than about 3, and most preferably less than about 2. Also, the adhesive filler is non-toxic. "Non-toxic", as used herein, means that the filler complies with the applicable acceptance limits and tests described in ADA specification No. 41. In addition, the adhesive filler should be essentially insoluble in mouth fluid. "Essentially insoluble", as used herein, refers to a filler whose solubility is sufficiently limited so that an orthodontic bracket adhesive containing such a filler will retain adequate strength in vivo, over the course of a typical orthodontic treatment (viz., up to 2 years), to prevent inadvertent early adhesive bond failure due to solubilization of the adhesive filler. In addition, it is desirable that the filler be non-discoloring in use, that is, the filler should not excessively stain or change color due to absorption of or reaction with other materials present in the adhesive, orthodontic brackets and tension wires, and mouth fluids.

The adhesive filler should represent greater than about 25 percent by weight of the total weight of the adhesive composition, preferably greater than about 35 percent by weight, and most preferably about 50 to 70 percent by weight. The adhesive filler should be finely divided in order to facilitate thorough mixing of the filler and the polymerizable resin. Preferably the filler particles have a mean diameter between about 1 and 100 micrometers and more preferably between about 1 and 20 micrometers.

Several suitable adhesive fillers are set out below in Table I. Data regarding chemical composition and hardness are from Hurlbut, Jr. and Klein, Manual of Mineralogy, 19th Ed., John Wiley & Sons, New York (1977), except where otherwise indicated.

TABLE I

| Adhesive filler | Composition | Mohs hardness |
|---|---|---|
| Aragonite | $CaCO_3$ | 3½–4 |
| Barite | $BaSO_4$ | 3–3½ |
| Boehmite | $AlO(OH)$ | 3½–4 |
| Calcite | $CaCO_3$ | 3 |
| Colemanite | $CaB_3O_4(OH)_3.H_2O$ | 4–4½ |
| Dolomite | $CaMg(CO_3)_2$ | 3½–4 |
| Fluorite | $CaF_2$ | 4 |
| Gibbsite | $Al(OH)_3$ | 2½–3½ |
| Hectorite | $(Mg,Li)_3Si_4O_{10}(OH)_2Na_{0.3}(H_2O)_4$ | 1–1½ |
| Hopeite* | $Zn_3(PO_4)_2.4H_2O$ | 3¼ |
| Kaolinite | $Al_2Si_2O_5(OH)_4$ | 2 |
| Langbeinite | $K_2Mg_2(SO_4)_3$ | 3½–4 |
| Montmorillonite | $(Al,Mg)_8(Si_4O_{10})_3(OH)_{10}.12H_2O$ | 1–1½ |
| Muscovite | $KAl_2(AlSi_3O_{10})(OH)_2$ | 2–2½ |
| Parisite* | $(Ce,La,Na,)FCO_3.CaCO_3$ | 4½ |
| Phlogopite | $KMg_3(AlSi_3O_{10})(OH)_2$ | 2½–3 |
| Pyrophyllite | $Al_2Si_4O_{10}(OH)_2$ | 1–2 |
| Scheelite | $CaWO_4$ | 4½–5 |
| Smithsonite | $ZnCO_3$ | 4–4½ |
| Sphalerite | $ZnS$ | 3½–4 |
| Talc | $Mg_3Si_4O_{10}(OH)_2$ | 1 |
| Vermiculite | $(Mg,Ca)_{0.3}(Mg,Fe,Al)_{0.3}(Al,Si)_4O_{10}(OH)_4.8H_2O$ | 1½ |
| Zincite | $ZnO$ | 4 |

*Handbook of Chemistry and Physics, 50th Ed., Chemical Rubber Co., Cleveland (1969).

Mixtures of more than one adhesive filler can be used in this invention. Kaolinite, mica, pyrophyllite, and talc are preferred adhesive fillers, with talc being most preferred. An asbestos-free California talc commercially available as "Cyprus C-400" from Cyprus Industrial Minerals Co., Talc Division, has been found to give very good results in this invention. This talc is noted for its light color due to the absence of graphite, a common talc contaminant. In addition, layers of this talc are held together by some ionic bonding in addition to the Van der Waals forces which hold most other talcs together. The additional interlayer bonding strength provided by ionic bonding decreases the lubricity of particles of "Cyprus C-400" talc and enhances the tensile and shear strength of an adhesive containing this talc.

The polymerizable resin can be any of the common resins used for orthodontic bracket adhesives. Such resins are generally two-part systems which cure when mixed, or one part systems which cure when exposed to light (e.g., actinic light or visible light). These resins are well known to those skilled in the art and need not be described in great detail herein, reference being made to U.S. Pat. Nos. 3,625,916, 3,629,187, 3,745,653, 3,955,282, 4,010,545, and 4,063,360, and to the examples set out below, for details regarding the chemical composition of suitable polymerizable resins. Preferably the adhesives of the present invention are formulated as two-part systems in which each part contains BIS-GMA and filler, together with a diluent/crosslinking agent such as triethyleneglycol dimethacrylate. In addition, one part of such a two-part system contains a free radical generating catalyst such as benzoyl peroxide, and the other part contains an accelerator such as dihydroxyethyl p-toluidine.

Mixing of the filler and polymerizable resin, as well as retention of the filler within the cured resin, can be improved if the filler is pre-treated with a surface modifying agent such as a silane compound, using methods well known in the art, such as those described for use with quartz restorative resin fillers in U.S. Pat. No. 3,066,112.

The orthodontic bracket adhesives of the present invention can also contain adjuvants such as conventional inhibitors, stabilizers, and pigments. Such adjuvants, if solids, preferably are no harder than tooth enamel and most preferably have a Mohs hardness less than that of the abrasives of this invention which are used to remove such adhesives. The use of adjuvants is not required in the adhesives of this invention, as useful adhesives can be prepared which consist of or consist essentially of non-toxic inorganic material having a Mohs hardness less than about 4.5 and polymerizable resin. It should be noted that it is current practice in the manufacture of orthodontic bracket adhesives to tint as orthodontic bracket adhesive so that its color closely matches tooth enamel. Although this may have cosmetic advantages, even an off-colored adhesive will remain largely unnoticed once it has been covered with brackets and tension wires. Complete removal of an adhesive which has been pigmented to match tooth color can be frustrated due to difficulty in visually detecting the adhesive. Orthodontists removing such adhesives inadvertently tend to leave excess adhesive on a tooth surface or grind away enamel in an effort to remove all the adhesive. It has been found that deliberate off-pigmentation of the adhesive, such as by addition of one to two weight percent of an opacifier having a Mohs hardness below about 4 such as calcium carbonate or zinc oxide, results in an adhesive whose appearance is not objectionable in use yet which can be readily visually detected and removed when treatment is completed. Opacifiers having a Mohs hardness above about 4 can also be used (e.g., titanium dioxide), but such hard opacifiers should not be added to the adhesive in amounts which would lead to damage of tooth enamel when the adhesive is removed with the abrasives of this invention. Preferably such hard opacifiers are not used in the adhesives of this invention in amounts greater than about 1 or 2 weight percent. Most preferably any opacifiers added to the adhesives of this invention have a Mohs hardness below about 5.

The orthodontic bracket adhesives of the present invention are mixed and applied to a tooth in the same manner as conventional bracket adhesives. Briefly, the method of applying such adhesives requires preliminary cleaning and etching of the tooth surface. This is performed by polishing the tooth surface with a dental prophylactic paste, rinsing, drying, etching the tooth surface for a few minutes with an acid etchant such as a 37 percent solution of orthophosphoric acid, followed by rinsing and drying the tooth. The prepared tooth surface will have a frosty white appearance.

Next, a thin layer of sealant resin, such as an unfilled BIS-GMA resin containing a catalyst and a diluent such as triethyleneglycol dimethacrylate, is applied to the prepared tooth surface and allowed to cure. This thin resin penetrates about 10 to 30 micrometers into the etched surface of the prepared tooth, aiding in formation of a strong adhesive bond and helping in prevention of subsequent decalcification of the enamel.

If a two-part orthodontic bracket adhesive is used, the two parts are next mixed on a palette. Light curable adhesives need not be mixed before use. A small quantity (about 15 to 20 mg) of adhesive is then applied as a layer to the prepared tooth surface, followed by placement of the bracket. The adhesive is then cured. Two-part adhesives are cured by allowing the mixed parts to stand undisturbed for about 30 seconds to about 5 minutes after application to the tooth surface. Light curable adhesives are cured by exposing the adhesive surface to suitable activating radiation and will cure within a few minutes. Curing of such light curable adhesives can be facilitated through use of translucent or perforated orthodontic brackets.

B. Abrasive

In addition to the adhesive described above, the present invention also provides an abrasive which removes the adhesive but does not damage tooth enamel. The second inorganic material (i.e. the abrasive) has a Mohs hardness greater than the Mohs hardness of the filler used in the bracket adhesive but less than about 5. Preferably the abrasive has a Mohs hardness less than about 4.5, in order to avoid damaging the enamel of even the softest teeth. Most preferably, the abrasive has a Mohs hardness well below that of enamel but more than about 1 Mohs hardness unit greater than the Mohs hardness of the adhesive filler. For example, if an adhesive filler with a Mohs hardness less than about 2 is used, then the abrasive used should have a Mohs hardness of about 3.

Also, the abrasive is non-toxic, but this requrement is less stringent than the toxicity requirement for the adhesive filler due to the brief patient exposure involved when such abrasives are used. In addition, it is desirable that the abrasive be essentially insoluble in mouth fluids, but this is not essential in the practice of this invention since the abrasive filler may be worn away in use and rinsed out of the mouth before it extensively dissolves.

The abrasive can be used in solid form as a scraping or cutting tool (such as a file, rasp, or knife) or the abrasive can be finely divided, mixed with a suitable solid binder, and formed into solid, shaped, composite tools such as files, rasps, or grinding attachments for standard powered dental tools. Such grinding attachments come in a variety of shapes but all have a central axis of symmetry and attaching means (such as a mandrel or an adhesive backing) for chucking them into a powered dental tool. Preferably the abrasives of this invention are used in the form of composite grinding attachments for a dental tool, because such attachments can be operated very rapidly, maximizing patient comfort and economizing on use of the orthodontist's time.

When the abrasive is in the form of a composite tool containing finely divided abrasive particles mixed with a binder, the binder can be any of the materials commonly used for dental abrasive tools of the prior art. These binders are well known to those skilled in the art and include materials such as phenolic resin and epoxies. Preferred binders for use in the present invention include cross-linked, rigid polymeric materials such as cured phenolic, epoxy, polyester, and polyurethane resins and soft materials such as silicone and neoprene rubbers.

Also, when the abrasive is in the form of a composite tool containing finely divided abrasive particles mixed with a bonder, the abrasive should represent greater than about 30% by weight of the total weight of abrasive and binder, preferably greater than about 50% by weight, and most preferably about 60 to about 70% by weight. The abrasive filler should be pulverized or comminuted in order to facilitate thorough mixing of the abrasive into the binder. Relatively large abrasive filler particles (e.g. 190 micrometers or greater mean diameter) are preferred, in order to yield a tool having a high cutting rate. It should be noted that this differs from current dental abrasive practice, where small diameter filler particles have been recommended in order to avoid causing deep scratches in tooth enamel.

In addition, where composite grinding attachments are prepared by finely dividing an abrasive, mixing it with a bonder, and coating the mixture onto a flexible backing such as a polymer web (e.g. in the production of small abrasive disks which will be coated with an adhesive backing and applied to a suitable mandrel), then the shape of the abrasive particles is important. It is preferred that such abrasive particles have shapes which are generally equiaxed, rather than acicular, fibrous, or otherwise excessively elongated. Using ordinary coating methods, elongated particles tend to align themselves with the plane represented by the web and become overcoated with binder resin. Abrasive disks made from such particles have poor abrasive ability. On the other hand, equiaxed particles tend to orient themselves randomly at the surface of the tool, and protrude through the binder surface, exposing optimum cutting edges. Abrasive disks made from such equiaxed particles have good abrasive ability, and can be more effective grinding attachments than attachments made from abrasive particles which are harder but elongated in shape.

Several suitable abrasives are set out below in Table II. Data regarding chemical composition and hardness are from Hurlbut, Jr. and Klien, Manual of Mineralogy, id, except where otherwise indicated.

TABLE II

| Abrasive filler | Composition | Mohs hardness |
| --- | --- | --- |
| Aragonite | $CaCo_3$ | $3\frac{1}{2}$–4 |
| Apatite | $Ca_5(PO_4)_3(F,Cl,OH)$ | 5 |
| Apophyllite | $KCa_4(Si_4O_{10})_2F \cdot 8H_2O$ | $4\frac{1}{2}$–5 |
| Barite | $BaSO_4$ | 3–$3\frac{1}{2}$ |
| Boehmite | $AlO(OH)$ | $3\frac{1}{2}$–4 |
| Calcite | $CaCO_3$ | 3 |
| Colemanite | $CaB_3O_4(OH)_3 \cdot H_2O$ | 4–$4\frac{1}{2}$ |
| Dolomite | $CaMg(CO_3)_2$ | $3\frac{1}{2}$–4 |
| Fluorite | $CaF_2$ | 4 |
| Gibbsite | $Al(OH)_3$ | $2\frac{1}{2}$–$3\frac{1}{2}$ |
| Hectorite | $(Mg, Li)_3Si_4O_{10}$—$(OH)_2Na_{0.3}(H_2O)_4$ | 1–$1\frac{1}{2}$ |
| Hemimorphite | $Zn_4(Si_2O_7)(OH)_2 \cdot H_2O$ | $4\frac{1}{2}$–5 |
| Hopeite* | $Zn_3(PO_4)_2 \cdot 4H_2O$ | $3\frac{1}{2}$ |
| Kaolinite | $Al_2Si_2O_5(OH)_4$ | 2 |
| Langbeinite | $K_2Mg_2(SO_4)_3$ | $3\frac{1}{2}$–4 |
| Marble | Predominately $CaCO_3$ | 3–4 |
| Muscovite | $KAl_2(AlSi_3O_{10})(OH)_2$ | 2–$2\frac{1}{2}$ |
| Parisite* | $(Ce,La,Na,)FCO_3 \cdot CaCO_3$ $FCO_3 \cdot CaCo_3$ | $4\frac{1}{2}$ |
| Phlogopite | $KMg_3(AlSi_3O_{10})(OH)_2$ | $2\frac{1}{2}$–3 |
| Scheelite | $CaWO_4$ | $4\frac{1}{2}$–5 |
| Smithsonite | $ZnCO_3$ | 4–$4\frac{1}{2}$ |
| Sphalerite | $ZnS$ | $3\frac{1}{2}$–4 |
| Wollastonite** | $CaSiO_3$ | 4–$5\frac{1}{2}$ |
| Zincite | $ZnO$ | 4 |

*Handbook of Chemistry and Physics, 50th Ed., Chemical Rubber Co., Cleveland (1969).
**Hurlbut and Klein list the hardness of Wollastonite as 5–$5\frac{1}{2}$. Values as low as 4 have been reported - see, e.g. Kraus, Hunt, and Ramsdell, Mineralogy Manual, McGraw Hill (1936), and 4.5 - see, e.g., U.S. Pat. No. 4,020,557.

Mixtures of more than one abrasive can be used in this invention. Calcite, dolomite, and marble are preferred abrasives, with marble being most preferred. A light-colored marble known as "white Georgia marble", a material having a Mohs hardness of about 3 and a composition which is approximately 97% $CaCO_3$/ 3% $MgCO_3$, has been found to give very good results in this invention. White Georgia marble is similar in chemical composition to calcite (pure crystalline $CaCO_3$) and dolomite (variable $CaCO_3/MgCO_3$ composition). White Georgia marble features with rhombohedral cleavage, and is especially effective when finely divided and mixed with a binder. The effect of abrasive particle shape may be further understood by noting that composite grinding attachments made by coating a mixture of finely divided white Georgia marble and a binder onto a web have a faster cutting rate than similar attachments made from harder but more elongated materials such as wollastonite. Wollastonite fractures with cleavage ranging from an acicular to a fibrous shape. As described above, such elongated particles tend to lie down on the web rather than protrude, and therefore are less effective as an abrasive than rhombohedral abrasive particles of white Georgia marble, even though wollastonite has a Mohs hardness of 4 to 5.5 while white Georgia marble has a Mohs hardness of 3. Other adjuvants (e.g., pigments) can also be used in the abrasives of this invention. Such adjuvants, if solid, preferably are no harder than tooth enamel. The use of adjuvants is not required in the abrasives of this invention, as useful abrasives can be prepared which consist of or consist essentially of non-toxic inorganic material having a Mohs hardness less than about 5 and solid binder.

The abrasives of this invention are typically used at the completion of orthodontic treatment of a tooth. An orthodontic bracket which has been adhered to the tooth by means of the adhesives described above is first removed from the tooth surface using orthodontic pliers or ligature cutters. Next, the residual adhesive remaining on the tooth surface is removed by grinding or scraping. Preferably residual adhesive is removed within as short a time as possible without excessive damage to the enamel. Complete removal within about 15 seconds can be regarded as a very satisfactory removal time.

It has been found that the abrasives of this invention are also useful in general dental work. These abrasives are surprisingly effective at rapidly cutting, polishing, and otherwise working dental composite materials filled with very hard fillers such as quartz (which has a Mohs hardness of about 7). Ordinarily, this would not be expected due to the low hardness of the abrasives in this invention and the high hardness of the fillers typically used in such dental composite materials. It is theorized that the abrasives of this invention cut into the polymerizable resins used in such dental composite materials, and the hard filler granules in those materials then fall or pop out. Accordingly, the abrasives of this invention used alone as a general tool for working composite dental materials such as dental restorative resin, acrylic teeth, and denture bases, constitute an additional aspect of this invention.

The present invention therefore provides an adhesive and abrasive useful for securing and removing orthodontic brackets. The adhesive has high strength good workability, and rapid set time. The adhesive can be deliberately off-pigmented in order to facilitate its observation and removal when treatment is completed. The abrasives of this invention can remove the above adhesive very rapidly, yet minimize damage to tooth enamel. After the use of such abrasives, no scratches can be detected on tooth enamel using a 15 power microscope.

The following examples are offered to aid understanding of the present invention and are not to be construed as limiting the scope thereof.

EXAMPLE 1

Pretreatment of Adhesive Filler

Gamma-methacryloxy-propyltrimethoxy-silane (2 gms) was mixed with glacial acetic acid (0.033 gms) and water (44.4 gms) in a plastic beaker. One hundred grams of talc ("Cyprus C-400", composed of particles having a mean diameter of 5 micrometers with 99.6% of the particles having a diameter less than 74 micrometers) was added and the mixture stirred for 1.5 hours at room temperature. The slurry was dried by warming it to 60° C. for 24 hours, followed by heating in an oven at 115° C. for 2.5 hours.

EXAMPLE 2

Preparation of Two-Part Adhesive

Two parts (A & B) of a BIS-GMA adhesive containing the silane-treated talc of Example 1 were prepared. Set out below in Table III are the composition of Part A and Part B, with all amounts expressed as parts by weight.

TABLE III

| Component | Part A | Part B |
|---|---|---|
| BIS-GMA resin | 28.60 | 29.16 |
| Triethyleneglycol-dimethacrylate | 9.03 | 9.21 |
| Silane-treated talc | 59.81 | 61.0 |
| Benzoyl peroxide | — | 0.47 |
| Dihydroxyethyl- | 0.88 | — |

TABLE III-continued

| Component | Part A | Part B |
|---|---|---|
| p-toluidine | | |
| 2(2'-hydroxy-5'-methylphenyl)-benzotriazole[a] | 0.31 | — |
| Phenylsalycilate-glycidylmethacrylate adduct (equimolar mixture) | 0.14 | 0.12 |
| Triphenylantimony | 0.04 | — |
| Butylated hydroxytoluene | — | 0.04 |
| Titanium dioxide | 1.19 | — |

[a] "Tinuvin P", commercially available from Geigy Industrial Chemical Corp.

Each part was prepared by mixing the BIS-GMA resin, triethylene glycol dimethacrylate, and any UV absorbers or inhibitors using a mixer such as an air stirrer. Accelerator was added to Part A and catalyst added to Part B. Separately, the treated talc and titanium dioxide pigments were dry mixed, then added to Part A and Part B with mixing.

The adhesive was tested using bovine teeth and a standard orthodontic bracket. A flat surface was ground into the enamel of a sample bovine tooth by wet grinding with 360 grit aluminum oxide coated abrasive paper. The surface was etched using 37% orthophosphoric acid for 2 minutes, followed by rinsing and drying. A thin layer of enamel bond resin ("Concise", commercially available from 3M) was applied to the dried etched surface and allowed to cure. Next, small, equal-volume samples of Parts A and B of the adhesive of this Example were applied to a palate and thoroughly mixed by manual spatulation. Thin layers of adhesive (approximately 15 to 20 milligrams of adhesive per tooth) were applied to the prepared, enamel bond coated surface, followed by attachment of a lateral meshed orthodontic bracket (Pad No. 065, Bracket No. 007, commercially available from American Orthodontics Co.). The bracket was held in place using hand pressure. The adhesive set in about 120 seconds and was fully cured after 10 minutes.

Fine orthodontic wire was attached to the bracket hooks, and the tooth and free wire end fastened in the jaws of an Instron tensile tester (Model No. 1122, Instron Corp.) set at a crosshead speed of 5 millimeters per minute and a chart drive speed of 50 millimeters per minute. The crosshead was advanced until the adhesive bond had failed in shear. The adhesive fractured at the interface between the adhesive and the bracket, a desirable fracture mode which minimized damage to the tooth. 17.5 kg were required to promote shear failure.

EXAMPLES 3-7

Testing of Additional Adhesive Fillers

Using the method of Examples 1 and 2, several fillers were substituted for the talc filler used in Examples 1 and 2. Set out below in Table IV are the example number, filler used, weight percent filler in the adhesive, and shear failure force.

TABLE IV

| Example No. | Filler | Weight % filler | Shear failure force, kg. |
|---|---|---|---|
| 3 | "Glomax LL" Kaolin[a] | 57% | — |
| 4 | "ASP No. 170" Kaolin[b] | 54.5% | 17.5 |
| 5 | "S.T. No. 1" Kaolin[c] | 55% | — |
| 6 | "Veecote" Pyrophyllite[d] | 58.5% | — |

TABLE IV-continued

| Example No. | Filler | Weight % filler | Shear failure force, kg. |
|---|---|---|---|
| 7 | Muscovite Mica[e] | 58% | — |

[a]Commercially available from Georgia Kaolin Co., Division of Yara Engineering Corp.
[b]Commercially available from Engelhard Minerals and Chemicals Corp.
[c]Commercially available from Engelhard Minerals and Chemicals Corp.
[d]Commercially available from R. T. Vanderbilt Co., Inc.
[e]Commercially available from Pacer Corp.

EXAMPLE 8

Marble Abrasive Disks

Five 50 gm portions of white Georgia marble chips (commercially available from Georgia Marble Company) were crushed and screened to the following size fractions in separate samples:
  600 to 425 micrometers
  425 to 250 micrometers
  250 to 150 micrometers
  150 to 106 micrometers
  106 to 74 micrometers.
Each sample was then mixed with a solution of 49 gms of "Bakelite PKHH" phenoxy resin (commercially available from Union Carbide Corp.) in 114 gms of methylethylketone, together with 1 gm of "PAPI 100" polymethylene polyphenylisocyanate (commercially available from Upjohn Co.). These ingredients were mixed by mechanical mixing and then knife coated (using a 171 micrometer gap) onto a silicon dioxide coated 190 micrometer thick polyester film (commercially available from Teledyne Post Inc.). The coated film was then oven cured for 2 hours at 79° C. 15.3 millimeter diameter disks were cut from the cured film, punctured through the center, and then fastened to a brass eyelet by inserting the eyelet through the punctured hole and staking the eyelet form a square hub. The resulting abrasive disks were fastened to a mandrel which had been mounted in a standard dental hand engine (No. 92N, commercially available from Teledyne Emesco Co.). Cured samples 6 mm×6 mm×37 mm in size prepared from the adhesives of Examples 1 through 7 were abraded for 15 seconds with the above abrasive disks, using average hand pressure and a rotational speed of 10,000 rpm. The fastest cutting rates were observed with disks made from large marble granules. A disk containing 425 to 600 micrometer abrasive particles removed 49 mg of the adhesive of Example 1. This data demonstrates that the abrasives of this invention rapidly remove the adhesives of this invention.

In a separate test, a 6 mm×6 mm×37 mm sample slug was prepared from a conventional quartz filled orthodontic bracket adhesive ("Concise 1960", commercially available from 3M). Under the test conditions described above, 12 mg of adhesive were ground away by a disk containing 425 to 600 micrometer abrasive particles. This illustrated that the abrasives of this invention could be used to cut and polish an orthodontic bracket adhesive filled with a material which is harder than the abrasives of this invention.

In a separate test, 6 mm×6mm×37 mm sample slug was prepared from a conventional quartz filled dental restorative resin ("Concise 1925", commercially available from 3M). Under the test conditions described above, 10 mg of restorative resin were ground away by a disk containing 425 to 600 micrometer abrasive particles. This illustrated that the abrasive disks of this invention could be used to cut and polish a dental restorative resin filled with a material which is harder than the abrasives of this invention.

EXAMPLE 9

Wollastonite Abrasive Disks

Using the method of Example 8, finely divided wollastonite ("Nycor 100", commercially available from Interpace Corp.) was combined with phenoxy resin binder and coated onto polyester film. Samples were tested as in Example 8. Again, the largest diameter particles gave highest cutting rates. However, using the same mesh size, wollastonite was roughly half as effective an abrasive as white Georgia marble.

EXAMPLE 10

Preparation of a Hard Abrasive Wheel 15 gms of white Georgia marble chips, sized on a sieve to 58 to 100 micrometers diameter, were mixed with a solution containing 80 gms of the phenoxy resin of Example 8 and 5 gms of polymethylene polymethylisocyanate. These ingredients were stirred to form a homogeneous mixture and poured into molds to make 13 mm diameter abrasive wheels having a thickness of 1.6 mm. The molded wheels were cured by heating in an oven for 30 minutes at 93° C. followed by heating for 14 hours at 60° C. The abrasive wheels were mounted in a powered dental hand tool and tested, using the method of Example 8, by abrading them against a 6 mm×6 mm×37 mm sample slug of cured adhesive prepared from the composition of Example 1, 15 second contact using average hand pressure at a rotational speed of 10,000 rpm removed 11.2 mgs of adhesive from the sample slug.

In a separate test, a 6 mm×6 mm×37 mm sample slug was prepared from "Concise 1925". Under the test conditions described above, 3.1 mg of restorative resin were ground away by the abrasive wheel. This illustrated that the abrasive wheels of this invention could be used to cut and polish a dental restorative resin filled with a material which is harder than the abrasives of this inventions.

EXAMPLE 11

Preparation of a Soft Rubber Abrasive Wheel

Fifty gms of white Georgia marble chips sized between 240 and 400 micrometers were combined with 50 gms of neoprene rubber (commercially available from Pawling Rubber Co.) on a 2 roll mill equipped with heat exchange means set at 12°-16° C. The milled mixture was formed into a 1.6 mm thick sheet and cured for 8 hours at 150° C. Soft wheels having a diameter of 13 mm were punched from the cured sheet.

The soft wheels were mounted on a mandrel and tested by abrading them against 6 mm×6 mm×37 mm sample slugs using the test conditions described in Example 8. The soft wheels removed 24 mg of the adhesive of Example 1, 17 mg of the adhesive of Example 4, and 14 mg of the adhesive of Example 6.

In a separate test, a 6 mm×6 mm×37 mm sample slug was prepared from "Concise 1960", quartz filled orthodontic bracket adhesives. Under the test conditions described above, 25 mg of bracket adhesive were ground away by the soft wheel.

Various modifications and alterations of this invention will be apparent to those skilled in the art without departing from the scope and spirit of this invention and the latter should not be restricted to that set forth herein for illustrative purposes.

What is claimed is:

1. A dental abrasive composition, comprising finely divided inorganic material admixed with a solid binder, said inorganic material being non-toxic, having a Mohs hardness less than about 5, and being in the form of generally equiaxed particles having a mean diameter of at least 190 micrometers, said inorganic material being at least 30% of the total weight of said composition, and said composition being in the form of a scraping tool, a cutting tool, or a grinding attachment for a standard powered dental tool, said tool having sufficiently low hardness to avoid damaging tooth enamel when used thereon.

2. A dental abrasive composition according to claim 1, wherein said inorganic material is selected from Table II.

3. A composition according to claim 1, wherein said inorganic material is at least 50% of the total weight of said composition.

4. A composition according to claim 1, wherein said inorganic material is about 60 to about 70% of the total weight of said composition.

5. A composition according to claim 1, wherein said inorganic material is selected from the group consisting of calcite, dolomite, and marble.

6. A composition according to claim 1, wherein said inorganic material comprises marble.

7. A composition according to claim 1, wherein said binder is a cross-linked, rigid polymeric material prepared from a resin selected from the group consisting of phenolic, epoxy, polyester and polyurethane resins.

8. A composition according to claim 7, in the form of a disk having a flexible backing.

9. A composition according to claim 1, wherein said binder is silicone or neoprene rubber.

* * * * *